(12) United States Patent
Oka et al.

(10) Patent No.: US 8,792,000 B2
(45) Date of Patent: Jul. 29, 2014

(54) IMAGE CAPTURING APPARATUS, IMAGE DISPLAYING METHOD AND RECORDING MEDIUM, IMAGE DISPLAYING PROGRAM BEING RECORDED THEREON

(75) Inventors: Kiyoshi Oka, Kizugawa (JP); Masahiro Edaya, Naka (JP)

(73) Assignees: Japan Atomic Energy Agency, Ibaraki (JP); Advanced Technology Co., Ltd., Ibaraki (JP)

( * ) Notice: Subject to any disclaimer, the term of this patent is extended or adjusted under 35 U.S.C. 154(b) by 755 days.

(21) Appl. No.: 12/882,680

(22) Filed: Sep. 15, 2010

(65) Prior Publication Data

US 2011/0074950 A1    Mar. 31, 2011

(30) Foreign Application Priority Data

Sep. 25, 2009   (JP) .................. 2009-220565

(51) Int. Cl.
| | |
|---|---|
| H04N 7/18 | (2006.01) |
| A61B 1/04 | (2006.01) |
| H04N 13/00 | (2006.01) |
| H04N 5/14 | (2006.01) |
| H04N 5/232 | (2006.01) |
| G06T 3/40 | (2006.01) |
| A61B 19/00 | (2006.01) |
| G01B 11/02 | (2006.01) |
| G01C 11/04 | (2006.01) |
| G02B 23/24 | (2006.01) |
| G06T 7/00 | (2006.01) |

(52) U.S. Cl.
CPC ......... *A61B 1/042* (2013.01); *A61B 2019/5231* (2013.01); *H04N 5/232* (2013.01); *G01B 11/022* (2013.01); *G01C 11/04* (2013.01); *G02B 23/2415* (2013.01); *G06T 7/0065* (2013.01); *G06T 2207/10072* (2013.01); *G06T 3/40* (2013.01)
USPC ................ 348/137; 348/45; 348/65; 348/699

(58) Field of Classification Search
CPC ........... A61B 1/042; A61B 2019/5231; H04N 5/232; G01B 11/022; G01C 11/04; G02B 23/2415; G06T 7/0065; G06T 2207/11072; G06T 3/40
See application file for complete search history.

(56) References Cited

U.S. PATENT DOCUMENTS 4,895,431 A * 1/1990 Tsujiuchi et al. ............... 359/29
5,432,543 A * 7/1995 Hasegawa et al. ............. 348/45

(Continued)

FOREIGN PATENT DOCUMENTS

| JP | 05-041901 | 2/1993 |
| JP | 2000-210248 | 8/2000 |

(Continued)

*Primary Examiner* — Joseph Ustaris
*Assistant Examiner* — Jill Sechser
(74) *Attorney, Agent, or Firm* — Brundidge & Stanger, P.C.

(57) ABSTRACT

An image capturing apparatus for capturing the image of the physical object and displaying the captured image is provided for combining and displaying in real time the shape-distorted graded scale with the captured image, the apparatus comprising a graded scale generating part for generating the graded scale to be used for indicating the dimension of the physical object in the captured image; a data storing part for storing the data for correction to be used in order to correct the graded scale shape by adding the distortion to the generated graded scale in the similar degree to the distortion caused by the distortion aberration; a graded scale shape correcting part for generating the shape-distorted graded scale by correcting the graded scale shape according to the data for correction; and an image combining part for combining the generated shape-distorted graded scale with the captured image, and displays the captured image combined with the shape-distorted graded scale.

5 Claims, 11 Drawing Sheets

(56) References Cited

U.S. PATENT DOCUMENTS 5,436,655 A * 7/1995 Hiyama et al. .................. 348/45
6,104,840 A * 8/2000 Ejiri et al. ..................... 382/284
2009/0259098 A1* 10/2009 Krattiger ...................... 600/109

FOREIGN PATENT DOCUMENTS

| JP | 2002-156212 | 5/2002 |
|----|-------------|--------|
| JP | 2005-087468 | 4/2005 |

* cited by examiner (a)

(b)

(a)

(b)

(a)  (b)

IMAGE CAPTURING APPARATUS, IMAGE DISPLAYING METHOD AND RECORDING MEDIUM, IMAGE DISPLAYING PROGRAM BEING RECORDED THEREON

BACKGROUND OF THE INVENTION

The present invention relates to a technology used in an image capturing apparatus which enables to capture the image of a physical object and display the captured image for displaying a graded scale to be used for indicating the dimension of the physical object so as to be displayed as an over layer onto the captured image.

In recent years, the image capturing apparatus to capture the image of the physical object under observation and to display the captured image in real time on the displaying part such as Liquid Crystal Display and organic/inorganic EL (electro-Luminescence) display has been widespread, for example, including endoscope, digital still camera and digital video camera. Such image capturing apparatus complete s imaging of the reflected light from the physical object as the object image on the imaging sensor such as CCD and CMOS by using the image capturing optical part comprising lens system, and then captures the completed object image.

The object image completed onto the imaging sensor using the image capturing optical part generally has a distortion in comparison with the actual physical object due to distortion aberration at the image capturing optical part. An example of distortion will be described by referring to FIG. 11 for better understanding.

FIG. 11 shows an illustration describing the distortion in the object image due to distortion aberration at the image capturing optical system. FIG. 11 (a) illustrates the actual physical object. FIG. 11 (b) illustrates the completed imaging of the physical object shown in FIG. 11 (a) by using the image capturing optical part having a barrel-shaped distortion aberration characteristic. As found in those figures, as the object image completed by the image capturing optical part has a distortion in comparison with the actual physical object, the captured image captured by the image capturing apparatus also becomes a distorted image in comparison with the actual physical object.

The barrel-shaped distortion as shown in FIG. 11 (b) is found in case that a wide-angle lens system is used as the image capturing optical part, and is also found to be significant in case that a wide-angle lens system is used for capturing the image at short range. As the wide-angle lens system has such a characteristic that the depth of field is larger and the image can be focused widely, it is often used in the endoscope in which it is structurally difficult to construct the image capturing optical part having the focus adjustment mechanism for driving multiple-lens systems. As the endoscope often captures the image of the physical object existing at the short range between several millimeters to dozens of centimeters, the above-described barrel-shaped distortion occurs significantly.

In case of capturing the image by using such imaging apparatus as described above, there raised a requirement from the user in order to recognize the actual dimension of the physical object in the captured image displayed at the displaying part. In order to meet such requirement, there is such a proposed technology that a plural of image capturing means for capturing the image of the physical object are provided at the endoscope, calculates the three-dimensional coordinates of the representative points in a plural of captured images on the basis of the positional relationship of those representative points, and then displays the graded scale as an over layer onto the captured image on the basis of the calculated three-dimensional coordinates (for example, refer to JP 2002-156212 A).

There is also such a proposed technology that, in the endoscope, an endoscope position and direction detecting means for calculating the spatial position and direction of the top of the endoscope, a displacement information working-out means for calculating the displacement of the endoscope image along the direction in the plane based on the movement of the individual points in the successive endoscope images, and a depth information working-out means for calculating the three-dimensional coordinates of those points in the endoscope image on the basis of the spatial position and direction of the top of the endoscope and the displacement of the endoscope image along the direction in the plane are provided, and then the graded scale is displayed on the basis of the calculated three-dimensional coordinates of those points (for example, refer to JP 2000-210248 A).

There is also such a proposed technology that, in the endoscope, a measurement light scanning means is provided, and then the distances between the individual points on the scan line of the laser light and the top of the endoscope are calculated, and then the graded scale is displayed on the basis of the calculated result (for example, refer to JP 05-041901 A (1998)).

There is also such a proposed technology that, in the endoscope, a distance image sensor is provided for capturing the range image representing the two-dimensional distribution of the distance-to-object, and then the graded scale is displayed on the basis of the calculated result (for example, refer to JP 2005-087468 A).

BRIEF SUMMARY OF THE INVENTION

There are such problems as described below by referring to Patent Literatures in the above proposed technologies.

In the proposed technology described in JP 2002-156212 A, it is required to detect the corresponding representative points in a plural of captured images captured by a plural of image capturing means. In order to detect the corresponding representative points in a plural of captured images, it is further required to calculate the correction values for compensating the distortion due to distortion aberration at the image capturing optical part for the individual captured images. As the computational complexity required in processing those calculations becomes extremely higher, it is difficult to display the graded scale in real time as an over layer onto the captured image in case of using a general purpose computer such as personal computers (hereinafter referred to as "PC") for processing those calculations.

In the proposed technology described in JP 2000-210248 A, the corresponding representative points in the successive captured images are detected, and then the three-dimensional coordinates of the individual corresponding representative points are calculated. Thus, as in the similar manner to the proposed technology described in Patent Literature 1, there is such a problem that the computational complexity becomes extremely higher and that it is difficult to display the graded scale in real time as an over layer onto the captured image in case of using a general purpose computer. In addition, as it is required to install the endoscope position and direction detecting sensor at the endoscope in order to detect the position of the top of the endoscope, there is such a problem that the price of the endoscope may become higher.

In the proposed technology described in JP 05-041901 A, the physical position of the laser light source is controlled by using the measurement light scanning means, and the laser light is scanned in the field of view of endoscope by switching sequentially the optical fibers to be used for guiding the laser light to the top of the endoscope, and thus, the distance-to-object along the scan line is calculated on the basis of the reflected laser light. Owing to this configuration, there is such a problem that a mechanism for controlling precisely the physical position of the laser light source is required, and thus, the structure of the image capturing apparatus becomes more complex.

In the proposed technology described in JP 2005-087468 A, as it is required to install the range image sensor for capturing the range image in order to calculate the three-dimensional positions of the individual points in the captured image, there is such a problem that the price of the image capturing apparatus becomes higher.

The object of the present invention is to provide an image capturing apparatus, an image displaying method and a recording media for recoding the program for displaying an captured image which enables to display the graded scale to be used as the index of the dimension of the physical object in real time as an over layer onto the captured image with inexpensive price and simplified structure.

In one aspect of the present invention, the image capturing apparatus comprises a light receiving part for receiving the reflected light reflected from the physical object;

an image capturing optical part for completing imaging as an object image by distorting the actual image of the physical object due to distortion aberration in response to the reflected light;

an image capturing part for capturing the object image as a captured image; and a displaying part for displaying the captured image, and further comprises a graded scale generating part for generating the graded scale to be used for indicating the dimension of the physical object in the captured image;

a data storing part for storing the data for correction to be used in order to correct the graded scale shape by adding the distortion to the generated graded scale in the similar degree to the distortion caused by the distortion aberration;

a graded scale shape correcting part for generating the shape-distorted graded scale by correcting the graded scale shape according to the data for correction; and an image combining part for combining the generated shape-distorted graded scale with the captured image, wherein the displaying part displays the captured image combined with the shape-distorted graded scale.

In another aspect of the present invention, the image displaying method, being performed by the image capturing apparatus comprising a light receiving part for receiving the reflected light reflected from the physical object; an image capturing optical part for completing imaging as an object image by distorting the actual image of the physical object due to distortion aberration in response to the reflected light; an image capturing part for capturing the object image as a captured image; and a displaying part for displaying the captured image, comprises:

a graded scale generating step for generating the graded scale to be used for indicating the dimension of the physical object in the captured image;

a graded scale shape correcting step for generating the shape-distorted graded scale by correcting the graded scale shape according to the data for correction to be used in order to correct the graded scale shape by adding the distortion to the generated graded scale in the similar degree to the distortion caused by the distortion aberration;

an image combining step for combining the generated shape-distorted graded scale with the captured image; and a step for displaying the captured image combined with the shape-distorted graded scale at the displaying part.

In further aspect of the present invention, the recording medium stores: the image displaying program instructing the image displaying method, being performed by the image capturing apparatus comprising a light receiving part for receiving the reflected light reflected from the physical object; an image capturing optical part for completing imaging as an object image by distorting the actual image of the physical object due to distortion aberration in response to the reflected light; an image capturing part for capturing the object image as a captured image; and a displaying part for displaying the captured image, to execute a graded scale generating procedure for generating the graded scale to be used for indicating the dimension of the physical object in the captured image;

a graded scale shape correcting procedure for generating the shape-distorted graded scale by correcting the graded scale shape according to the data for correction to be used in order to correct the graded scale shape by adding the distortion to the generated graded scale in the similar degree to the distortion caused by the distortion aberration;

an image combining procedure for combining the generated shape-distorted graded scale with the captured image; and a procedure for displaying the captured image combined with the shape-distorted graded scale at the displaying part.

The present invention is characterized as generating the graded scale to be used for indicating the dimension of the physical object in the captured image; correcting the graded scale shape by adding the distortion to the generated graded scale in the similar degree to the distortion caused by the distortion aberration at the image capturing optical part; and displaying the corrected shape-distorted graded scale as an over layer onto the captured image. According to the present invention, as the graded scale shape is corrected by adding the distortion to the generated graded scale in the similar degree to the distortion caused by the distortion aberration, it will be appreciated that the computational complexity can be smaller that the case of applying the shape correction to the captured image, and that the graded scale can be displayed in real time as an over layer onto the captured image even by using the general purpose computer such as PCs.

According to the present invention, it will be appreciated that the image capturing apparatus may be provided with inexpensive price because there is no need for any endoscope position and direction sensor as disclosed in Patent Literature 3 or any special sensor such as range image sensor disclosed in Patent Literature 4.

According to the present invention, it will be also appreciated that the image capturing apparatus may be provided with a simplified structure because there is no need for any complex structure for controlling precisely the physical position such as the measurement light scanning means disclosed in Patent Literature 3.

DESCRIPTION OF THE PREFERRED EMBODIMENTS

Referring to the attached figures, the best mode for carrying the invention will now be described below.

First Embodiment

Figure 1:
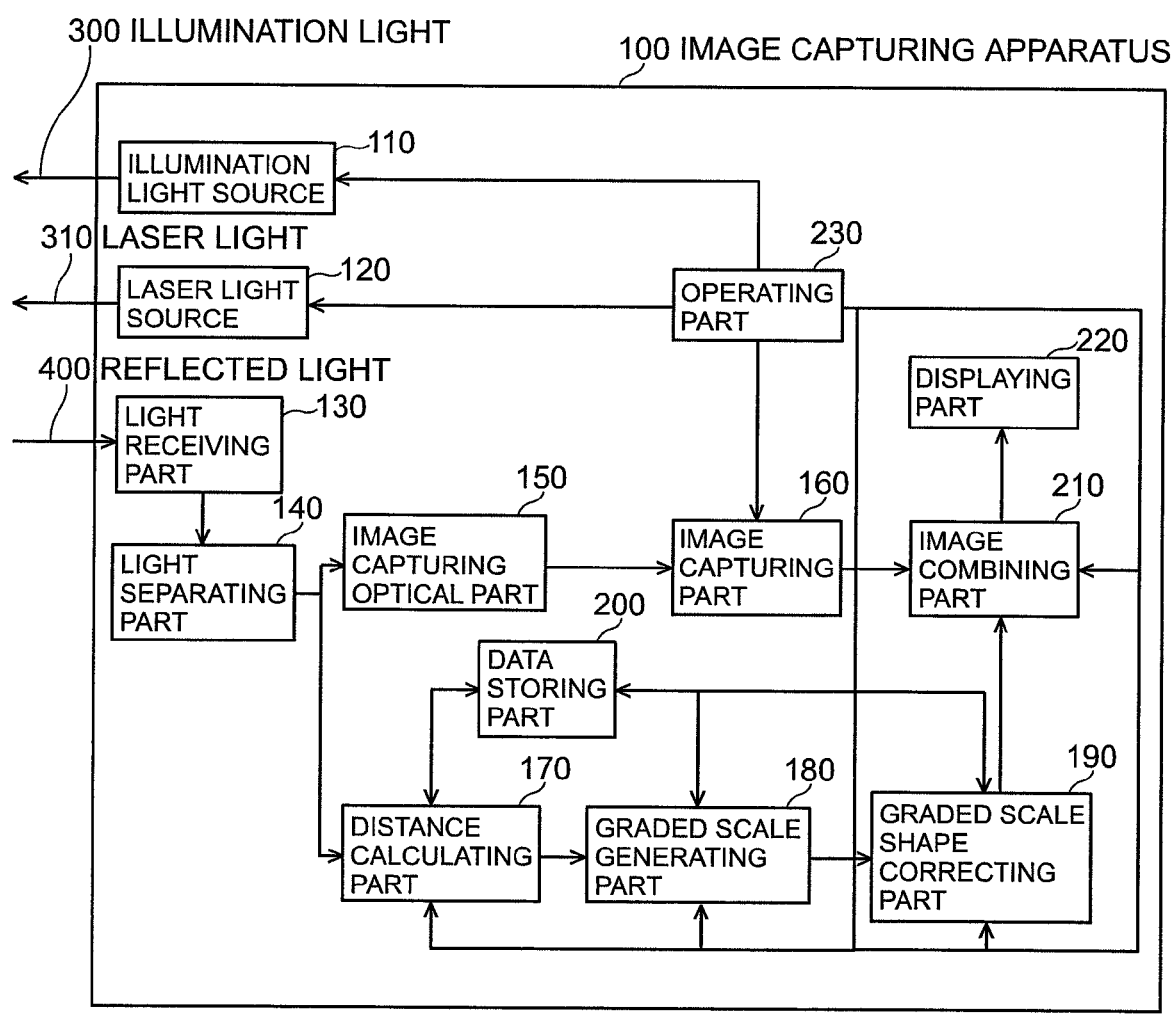
FIG. 1 is a block diagram showing the structure of the image capturing apparatus in the first embodiment according to the present invention.

FIG. 1 is a block diagram showing the structure of the image capturing apparatus of the first embodiment according to the present invention. As shown in FIG. 1, the image capturing apparatus 100 in this embodiment comprises the illumination light source 110, the laser light source 120, the light receiving part 130, the light separating part 140, the image capturing optical part 150, the image capturing part 160, the distance calculating part 170, the graded scale generating part 180, the graded scale shape correcting part 190, the data storing part 200, the image combining part 210, the displaying part 220 and the operating part 230.

The illumination light source 110, receiving the instruction issued from the operating part 230 for irradiating the illumination light, starts irradiating the light including at least a part of the wavelength region of the visible light (from 380 nm to 750 nm) or its full wave length region of the visible light as the illumination light 300 projected onto the physical object. A xenon lamp or a halogen lamp can be used for the illumination light source 110.

The laser light source 120, receiving the instruction issued from the operating part 230 for irradiating the laser light, starts irradiating the laser light 310 projected onto the physical object. In this embodiment, the laser light source 120 may irradiate a laser light having the wave length of 780 nm. As in this embodiment in which the laser light having the wave length region outside the wave length region of the visible light is used, it can be avoided that the laser light 310 might interfere into the captured image of the physical object captured at the image capturing part 160. It should be noted that the wave length region of the laser light 310 to be irradiated by the laser light source 120 may not be limited to the region described above but the laser light having an arbitrary light wave region may be used.

The light receiving part 130 receives the reflected light 400 including the irradiated light 300 and the laser light 310, both reflected at the physical object. Assuming that an endoscope is used for example as the image capturing apparatus 100, the light receiving part 130 corresponds to the top part of the endoscope.

The light separating part 140 separates the reflected light 400 received at the light receiving part 130 into the light component of the laser light 310 (laser light component) and the other light component (illumination light component) including the illumination light 300 component. The illumination light component separated by the light separating part 140 is injected into the image capturing optical part 150, and the laser light component is injected into the distance calculating part 170, respectively. Note that a beam splitter such as dichroic prism may be used for the light separating part 140.

The image capturing optical part 150, based on the illumination light component injected by the light separating part 140, completes imaging of the physical object as the object image at the image capturing part 160. The image capturing optical part 150 has its own intrinsic distortion aberration, and hence, the completed object image is distorted in relative to the actual physical object. Note that a wide-angle lens may be used for the image capturing optical part 150.

The image capturing part 160, in response to the instruction issued by the operating part 230 for initiating the image capturing, captures the object image completed by the image capturing optical part 150 and thus as the captured image. In this embodiment, the image capturing part 160 is so configured to repeat the capturing operation of the completed object image on the basis of the predefined frame rate for capturing images. Note that an imaging sensor such as CCD and CMOS may be used for the image capturing part 160.

The distance calculating part 170, in response to the instruction issued by the operating part 230 for initiating the graded scale generation, calculates the distance-to-object indicating the distance between the light receiving part 130 and the physical object, based on the laser light component injected by the light separating part 140. In this embodiment, the distance calculating part 170 is so configured to repeat the calculation of the distance-to-object on the basis of the predefined frame rate for capturing images at the image capturing part 160.

The graded scale generating part 180, based on the distance-to-object calculated at the distance calculating part 170, calculates the pitch in the graded scale to be used as the index of the dimension of the physical object in the image captured at the image capturing part 160, and then generates the graded scale according to the calculated pitch. Note that the graded scale generating part 180 generates the graded scale every time when the distance-to-object is calculated at the distance calculating part 170.

The graded scale shape correcting part 190 generates the shape-distorted graded scale by correcting the shape of the graded scale by way of adding the distortion to the graded scale generated by the graded scale generating part 180 in the similar degree to the distortion caused by the distortion aberration at the image capturing optical part 150. Note that the graded scale shape correcting part 190 generates the shape-distorted graded scale every time when the graded scale is generated at the graded scale generating part 180.

The data storing part 200 stores the data used for correction such as correction parameters and correction matrices to be used for calculating the distance-to-object at the distance calculating part 170, calculating the pitch in the graded scale at the graded scale generating part 180, and correcting the shape of the graded scale at the graded scale shape correcting part 190. Those data values are so configured to be enabled to be modified from the operating part 230 through the distance calculating part 170, the graded scale generating part 180, and the graded scale shape correcting part 190 and so on.

The image combining part 210 combines the shape-distorted graded scale generated by the graded scale shape correcting part 190 as an over layer with the image captured at the image capturing part 160, and outputs the combined captured image to the displaying part 220. Note that, in case of the operating part 230 not accepting the instruction for initiating the graded scale generation, the image combining part 210 may not combine the shape-distorted graded scale with the captured image but output only the captured image provided by the image capturing part 160 directly to the displaying part 220. The operating part 230 accepts the various instructions by the user as described above and then transfers those instructions to the individual structural components.

Figure 2:
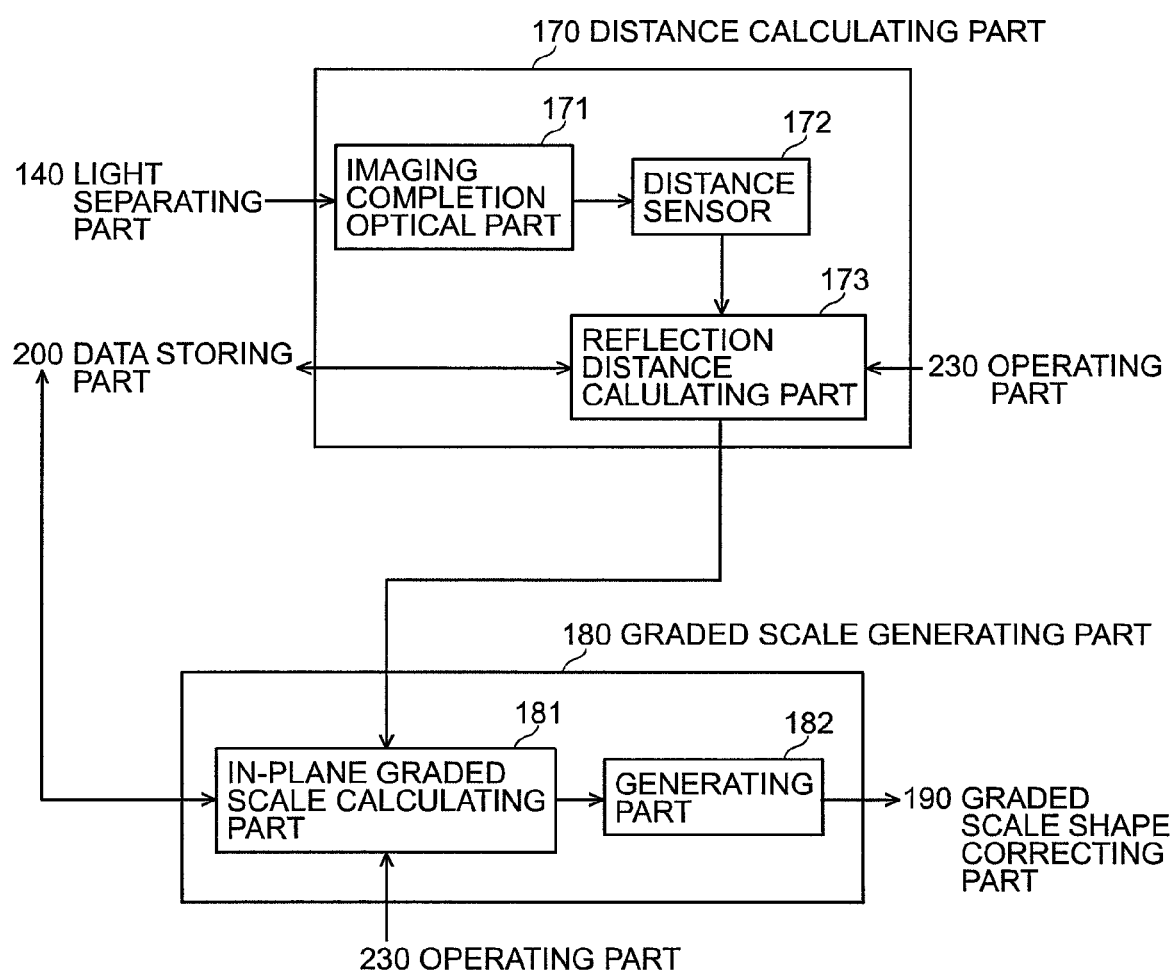
FIG. 2 is a block diagram of the detail structure of the distance calculating part 170 and the graded scale generating part 180 shown in FIG. 1.

Next, referring to FIG. 2, the configuration of the distance calculating part 170 and the graded scale generating part 180 will be now described in detail. FIG. 2 is a block diagram showing a detail structure of the distance calculating part 170 and the graded scale generating part 180, both shown in FIG. 1.

At first, the structure of the distance calculating part 170 will be described. As shown in FIG. 2, the distance calculating part 170 comprises the imaging completion optical part 171, the distance sensor 172 and the reflection distance calculating part 173. The imaging completion optical part 171 focuses the laser light component injected from the light separating part 140 onto the distance sensor 172. The distance sensor 172 measures the light income indicating the intensity of the laser light component converged by the imaging completion optical part 171. As in the similar manner to the image capturing part 160, an imaging sensor such as CDD and CMOS may be used as the distance sensor 172. The reflection distance calculating part 173, in response to the instruction from the operating part 230 for initiating the graded scale generation, calculates the distance-to-object based on the light income of the laser light component measured by the distance sensor 172 and the distance calibration parameters stored in the data storing part 200. Note that the reflection distance calculating part 173 is so configured to repeat the distance-to-object calculation on the basis of the predefined frame rate for capturing images at the image capturing part 160.

The technique for calculating the distance-to-object from the light income of the laser light component is well known to those skilled in the art, which uses the technology based on the physical phenomena in which the longer the distance-to-object, the smaller the light income of the laser light component. As the light income of the laser light component decreases exponentially in relative to the distance-to-object, it will be appreciated that the distance-to-object can be estimated from the light income of the laser light component by looking up a set of distance calibration parameters on the approximate curve prepared by measuring the light income of the laser light component at the relevant sets of distance-to-object.

Next, the structure of the graded scale generating part 180 will be described. As shown in FIG. 2, the graded scale generating part 180 comprises the in-plane graded scale calculating part 181 and the generating part 182.

The in-plane graded scale calculating part 181, based on the distance-to-object calculated at the reflection distance calculating part 173 and the in-plane graded scale pitch parameters stored in the data storing part 200, calculates the pitch in the graded scale to be used as the index of the dimension of the physical object in the image captured at the image capturing part 160. In this embodiment, the graded scale pitch parameters indicate the relationship between the distance-to-object and the pitch in the graded scale to be generated, which can be obtained by associating the individual distance-to-object measured in terms of constant distance in the actual three-dimensional space with the number of pixels in the captured image. Note that the pitch of the graded scale calculated at the in-plane graded scale calculating part 181 is defined to be the pitch of the in-plane graded scale indicating the dimension of the physical object on the identical plane placed at the depth in the captured image equivalent to the distance-to-object. This pitch of the graced scale is hereinafter referred to as "the in-plane pitch of the graded scale". The generating part 182 generates the in-plane graded scale based on the in-plane pitch of the graded scale so calculated at the in-plane graded scale calculating part 181, and then outputs it to the graded scale shape correcting part 190.

Figure 3:
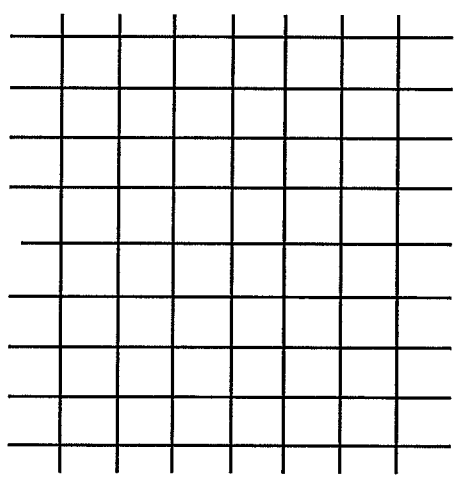
FIG. 3 is an illustration describing the operation of the graded scale shape correcting part 190 shown in FIG. 1
Figure 3:
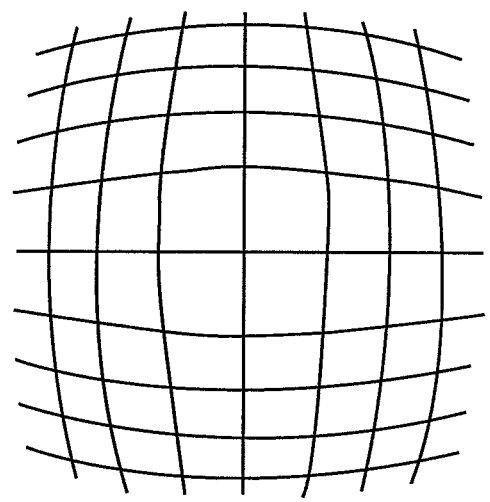

FIG. 3 is an illustration for describing the operation of the graded scale shape correcting part 190 shown in FIG. 1. In this embodiment, FIG. 3 (*a*) shows an example of the graded scale generated by the graded scale generating part 180, and FIG. 3(*b*) shows an example of the shape-distorted graded scale generated by the graded scale shape correcting part 190, respectively.

The graded scale shape correcting part 190 generates the shape-distorted graded scale as shown in FIG. 3 (*b*), by applying the geometrical transformation as shape correction to the graded scale as shown in FIG. 3 (*a*) generated by the graded scale generating part 180 using the correction parameters and the correction matrices as correction data stored in advance at the data storing part 200. In this embodiment, the correction parameters and the correction matrices as correction data include parameters and matrices representing the geometrical transformation for applying the similar degree of distortion in the object image caused by the distortion aberration at the image capturing optical part 150 to the generated graded scale.

The correction parameters and the correction matrices can be obtained by calculation based on the distortion in the given lattice pattern, for example, checkered pattern, captured by the image capturing optical part 150. More specifically, this calculation includes applying at first the known technology such as Zhang method for obtaining the correction parameters and the correction matrices from the image of the given lattice pattern captured by the image capturing optical part 150 to be used for applying the geometrical correction in order to correct the distortion caused by the by the distortion aberration at the image capturing optical part 150, and calculating next their inverse transformations in terms of correction parameters and correction matrices.

Note that the same method as the geometrical transformation method in the known technology such as Zhang method described above may be used for the geometrical transformation method using the correction parameters and the correction matrices. In addition, it is allowed that the correction parameters and the correction matrices used as correction data, which have characteristic values inherent to the image capturing optical part 150, may be calculated when the image capturing apparatus 100 in this embodiment is manufactured, and may be stored as initial configuration data at the data storing part 200.

Thus, it will be appreciated that the dimension of the physical object in the captured image can be obtained on the basis of the shape-distorted graded scale by combining the shape-distorted graded scale generated as described above as an over layer with the captured image at the image combining part 210 and then displaying the combined image at the displaying part 220. Though this embodiment is illustrated as shown in FIG. 3 (a) in which the graded scale generating part 180 generates a lattice-like scale on the basis of the calculated pitch of the graded scale, it is allowed to generate another kind of graded scale such as cross-hair and straight line. Though this embodiment is also illustrated as shown in FIG. 3(b) in which the image capturing optical part 150 provides intrinsically a barrel-shaped distortion aberration, it is allowed to provide another kind of distortion aberration such as bobbin winder distortion aberration.

Figure 4:
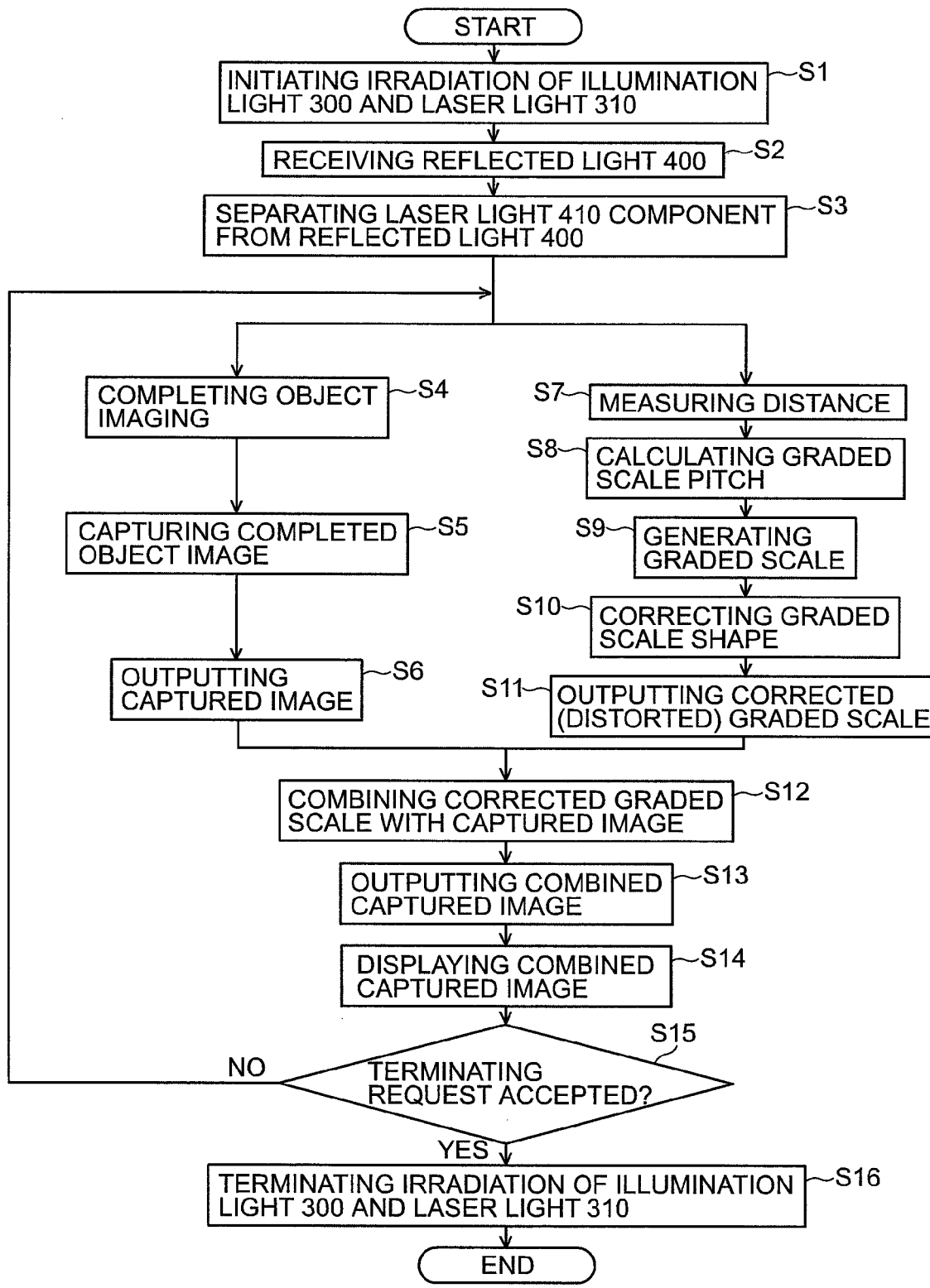
FIG. 4 is a flowchart describing the operation of the image capturing apparatus shown in FIG. 1.

Referring to FIG. 4, the operation of the image capturing apparatus 100 shown in FIG. 1 will now be described. FIG. 4 is a flow chart describing the operation of the image capturing apparatus 100 shown in FIG. 1.

At first, when the user of the image capturing apparatus 100 operates at the operating part 230 to instruct for irradiating the illumination light 300 and the laser light 310, the illumination light source 110 and the laser light source start irradiating the illumination light 300 and the laser light 310, respectively (Step S1).

Next, when the user operates at the operating part 230 to instruct for initiating the image capturing and the graded scale generation, the image capturing part 160 starts capturing the images and the distance calculating part 170 starts calculating the distance-to-object, respectively. Upon starting the irradiation of the illumination light 300 and the laser light 310, the reflected light 400 reflected from the physical object is received at the light receiving part 130 (Step S2).

The reflected light 400 received at the light receiving part 130 is separated at the light separating part 140 into the illumination light component and the laser light component, and then the illumination light component is injected into the image capturing optical part 150, and the laser light component is injected into the imaging completion optical part 171 at the distance calculating part 170, respectively (Step S3)

Upon the illumination light component injected into the image capturing optical part 150, the image capturing optical part 150 completes imaging of the physical object as the object image based on the illumination light component at the image capturing part 160 (Step S4). In this step, the object image has a distortion in comparison with the actual physical object due to distortion aberration at the image capturing optical part 150.

The image capturing part 160 which already starts capturing the image upon instruction from the operating part 230 captures the completed object image and outputs the captured image to the image combing part 210 (Steps S5 and S6).

At the same time, upon the laser light component injected into the imaging completion optical part 171, the imaging completion optical part 171 converges the laser light component onto the distance sensor 172. The distance sensor 172 measure the light income of the laser light component converged by the imaging completion optical part 171, and outputs the measured light income to the reflection distance calculating part 173. The reflection distance calculating part 173 which already starts calculating the distance-to-object calculates the distance-to-object based on the light income measured by the distance sensor 172, and outputs the calculated distance-to-object to the in-plane graded scale calculating part 181 at the graded scale generating part 180 (Step S7).

The in-plane graded scale calculating part 181 calculates the pitch of the in-plane graded scale based on the distance-to-objected calculated at the reflection distance calculating part 173 and the calibration parameter for the pitch of the graded scale stored in the data storing part 200 (Step S8).

The generating part 182 generates the in-plane graded scale based on the pitch of the in-plane graded scale calculated at the in-plane graded scale calculating part 181 (Step S9).

The graded scale shape correcting part 190 generates the shape-distorted graded scale by correcting the shape of the graded scale generated at the generating part 182 on the basis of the correction matrices stored in the data storing part 200, and then outputs the shape-distorted graded scale to the image combining part 210 (Steps S10 and S11).

Next, the image combining part 210 combines the shape-distorted graded scale output from the graded scale shape correcting part 190 as an over layer with the captured image output from the image capturing part 160, and then outputs the combined captured image to the displaying part 220 (Steps S12 and S13).

Next, the displaying part 220 displays the captured image combined with the shape-distorted graded scale output from the image combining part 210 (Step S14).

Steps S4 to S14 are repeated at the frame rate for capturing images at the image capturing part 160 until the user operates at the operating part 230 to instruct for terminating capturing images and generating the graded scale. Upon the user's operation at the operating part 230 for instructing for terminating capturing images and generating the graded scale, the image capturing part 160 terminates capturing images and the reflection distance calculating part 173 terminates calculating the distance-to-object (Step S15).

Thereafter, when the user operates at the operating part 230 to instruct for terminating the irradiation of the illumination light 300 and the laser light 310, the illumination light source 110 and the laser light source 120 terminate the irradiation of the illumination light 300 and the laser light 310, respectively (Step S16).

The effect of this embodiment will be now described below.

As described above, the image capturing apparatus 100 in this embodiment generates the graded scale to be used as the index of the dimension of the physical object in the captured image, corrects the shape of the generated graded scale by way of adding the distortion to the generated graded scale in the similar degree to the distortion caused by the distortion aberration at the image capturing optical part 150, and then combines the corrected shape-distorted graded scale with the captured image and finally displays them as overlapped layers.

As the image capturing apparatus 100 in this embodiment applies the shape correction only to the generated graded scale, its computational complexity is less than the case of applying the shape correction to the captured image itself, and that the graded scale can be displayed in real time as an over layer onto the captured image even by the general purpose computer such as PC.

As the image capturing apparatus 100 in this embodiment does not require special sensors such as distance image sensor disclosed in Patent Literature 4 and endoscope position and direction detecting means disclosed in Patent Literature 2, it can be provided with an inexpensive price.

As the image capturing apparatus 100 in this embodiment does not require such a complex structure for controlling precisely the physical position as the measurement light scanning means disclosed in Patent Literature 3, it can be realized with a simplified configuration.

As the image capturing apparatus 100 in this embodiment calculates the distance-to-object based on the laser light component as included in the reflected light of the laser light 310, and then generates the graded scale corresponding to the distance-to-object by calculating the pitch of the in-plane graded scale based on the calculated distance-to-object, it can display the graded scale having an adequate pitch as an over layer onto the captured image even if the dimension of the physical object projected in the captured image may change due to the deviation in the distance-to-object.

Embodiment 2

Figure 5:
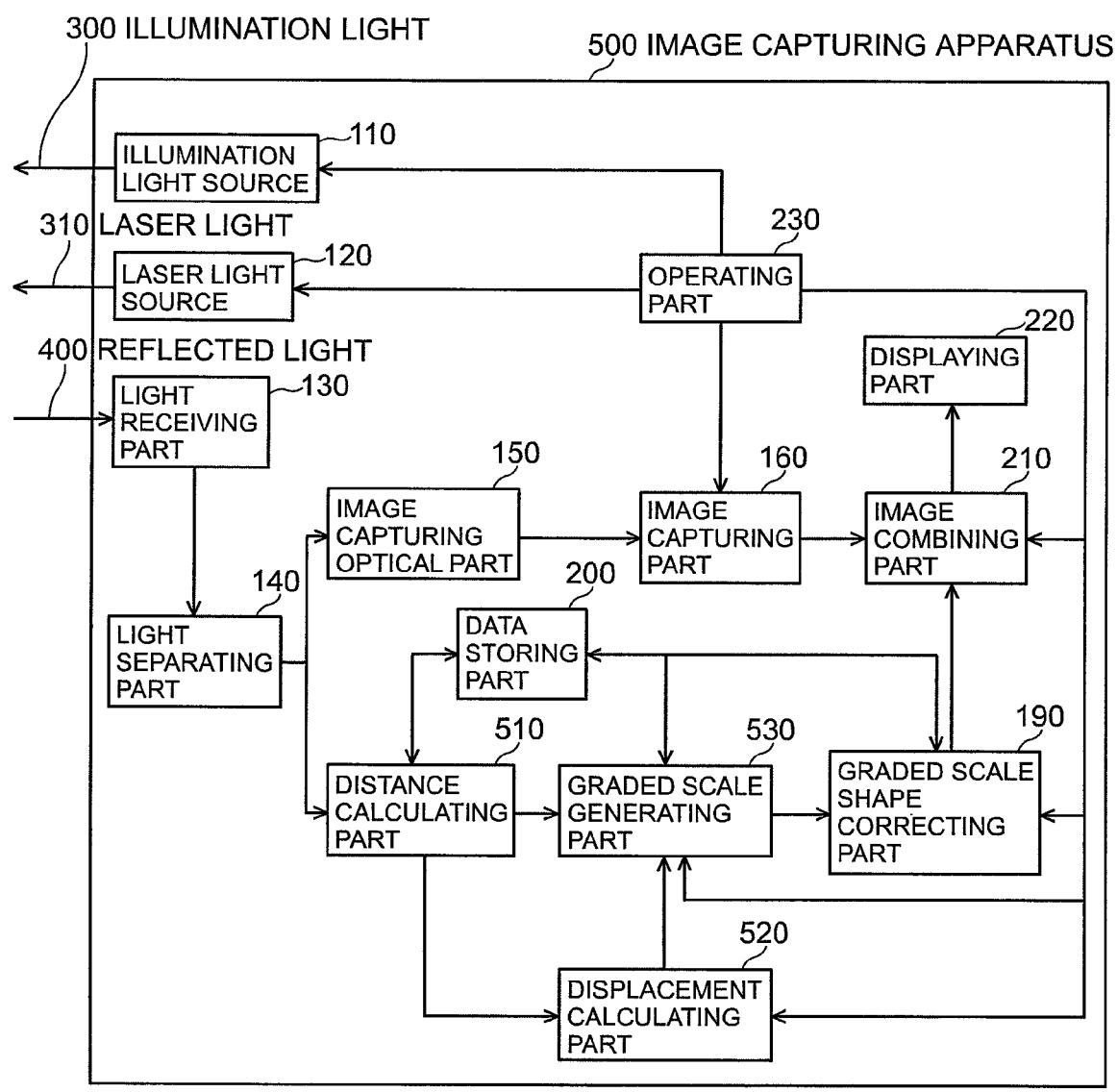
FIG. 5 is a block diagram showing the structure of the image capturing apparatus in the second embodiment according to the present invention.
Figure 6:
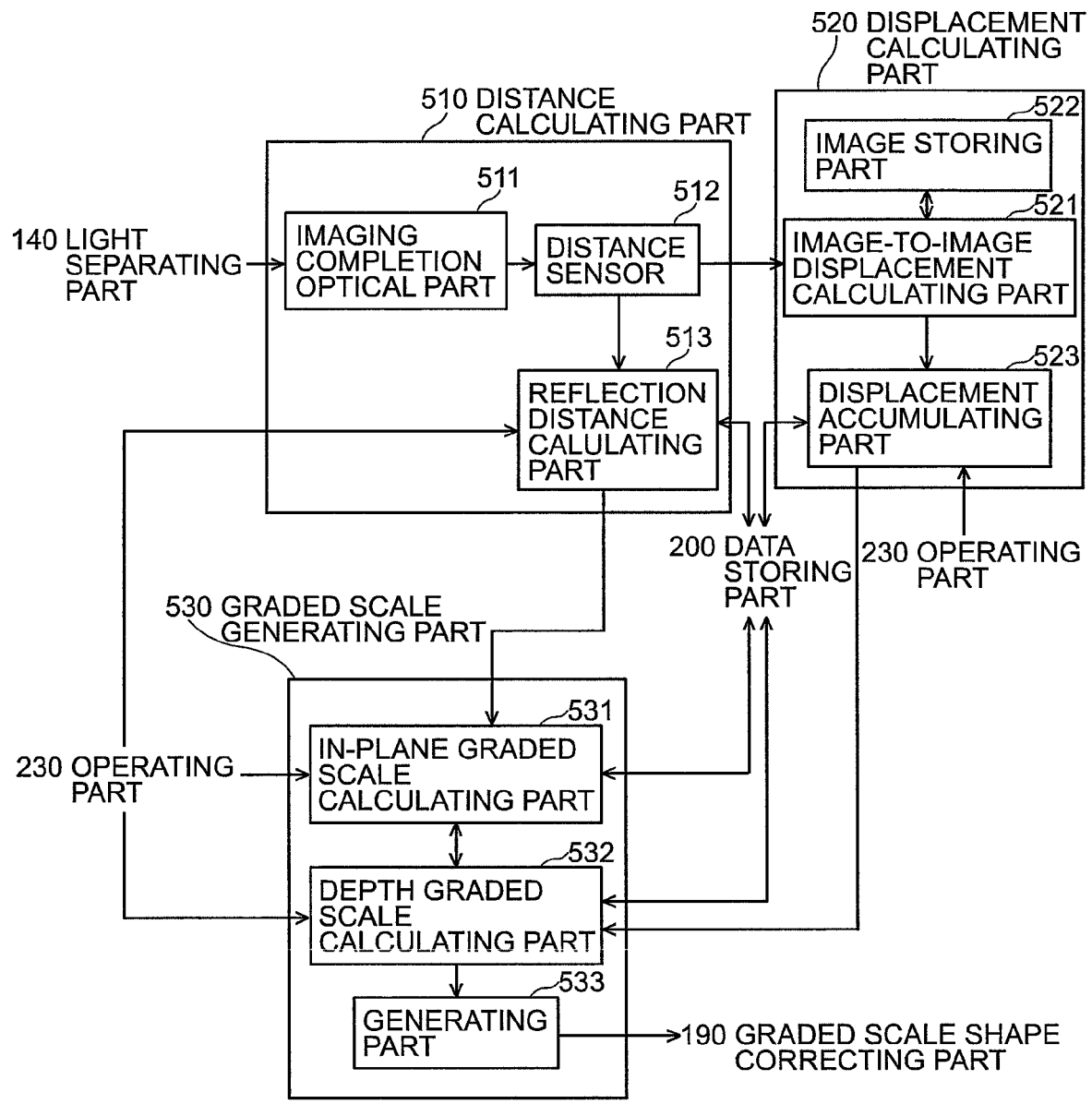
FIG. 6 is a block diagram showing the detail structure of the distance calculating part 510, the displacement calculating part 520 and the graded scale generating part 530 shown in FIG. 5.

FIG. 6 is a block diagram showing the structure of the image capturing apparatus of the second embodiment according to the present invention. As shown in FIG. 5, the image capturing apparatus 500 in this embodiment has such differences from the image capturing apparatus 100 of the first embodiment as shown in FIG. 1 as the displacement calculating part 520 is added, and the distance calculating part 170 is replaced by the distance calculating part 510, and the graded scale generating part 180 is replaced by the graded scale generating part 530. Note that other structural elements are the same as those in the image capturing apparatus 100 shown in FIG. 1 and they will not be described in detail.

FIG. 6 is a block diagram describing the detail structure of the distance calculating part 510, the displacement calculating part 520 and the graded scale generating part 530 shown in FIG. 6. As shown in FIG. 6, the distance calculating part 510 has the imaging completion optical part 511, the distance sensor 512 and the reflection distance calculating part 513.

The imaging completion optical part 511 completes imaging of the speckle pattern as the speckle image developed on the physical object by irradiating the laser light 310 based on the laser light component injected from the light separating part 140. Note that a wide-angle lens may be used as the imaging completion optical part 511.

The distance sensor 512 measures the light income of the laser light component in the similar manner to the distance sensor 172 shown in FIG. 2. The distance sensor 512 also captures the speckle image completed at the imaging completion optical part 511. The distance sensor 512 is so configured to repeat capturing the speckle image on the basis of the predefined frame rate, and then the captured speckle image is output to the displacement calculating part 520. Note that the frame rate for capturing the speckle image may be equal to or higher than the frame rate for capturing images at the capturing part 160. Note also that an imaging sensor such as CCD and CMOS may be used as the distance sensor 512. The reflection distance calculating part 513 is the same as the reflection distance calculating part 173 shown in FIG. 2, which will not be described here.

The structure of the displacement calculating part 520 will now be described. As shown in FIG. 6, the displacement calculating part 520 comprises the image-to-image displacement calculating part 521, the image storing part 522 and the displacement accumulating part 523.

The image storing part 522 is a storing area dedicated for the image-to-image displacement calculating part 521, which can support data read/write operations faster than the data storing part 200 does.

The image-to-image displacement calculating part 521 calculates the displacement between successive speckle images captured at the distance sensor 514. More specifically, the image-to-image displacement calculating part 521 stores the speckle images output from the distance sensor 512 at the image storing part 522. The image-to-image displacement calculating part 521 also calculates the vector representing the displacement between the speckle image output from the distance sensor 512 and the speckle image output at the previous cycle by the distance sensor 512 and stored in the image storing part 522. Note that the image-to-image displacement calculating part 521 calculates the displacement between the speckle images based on the known calculating method, for example, such as the method for calculating the correlation between the speckle images, the method for calculating the optical flow, and the method for calculating the SHIFT (Scale Invariant feature transform) feature quantity and so on. Such technologies for calculating the displacement between the speckle images will not be described in detail, which are known to those in the art, for example, used in the laser mouse. Note that, though the speckle image is stored at the image storing part 522 in the image-to-image displacement calculating part 512 in this embodiment, it is allowed to store them at the data storing part 200.

The displacement accumulating part 523 accumulates the displacement calculated at the image-to-image displacement calculating part 512 during a predetermined period of time, and outputs the accumulated value of the displacement as the displacement of the light receiving part 130 in a predetermined period of time to the graded scale generating part 530. Note that the predetermined period of time may be equal to or longer than the time corresponding to the frame rate for capturing images at the capturing part 160. Note that, though the displacement accumulating part 523 is so configured to accumulate the displacement during a predetermined period of time, its configuration is not limited to this one. For example, it is allowed that the displacement may be accumulated from the time when the operating part 130 accepts the instruction indicating the start of the light receiving part 130 moving until the time when it accepts the instruction indicating the end of movement. Note that the displacement is calculated as the vector, which represents mathematically the accumulated amount of displacement in terms of vector.

The structure of the graded scale generating part 530 will now be described. As shown in FIG. 6, the graded scale generating part 530 comprises the in-plane graded scale calculating part 531, the depth graded scale calculating part 532 and the generating part 533.

The in-plane graded scale calculating part 531, upon the distance-to-object being output from the reflection distance calculating part 513, calculates the pitch of the in-plane graded scale based on the distance-to-object and the graded scale pitch parameter stored at the data storing part 200, and then outputs the calculated pitch of the in-plane graded scale and the distance-to-object to the depth graded scale calculating part 532.

The depth graded scale calculating part 532, upon the displacement of the light detecting part 130 being output from the displacement accumulating part 523, calculates the pitch of the depth graded scale to be used as the index of the dimension of the physical object in the captured image, based on the displacement, the distance-to-object calculated by the distance calculating part 510 at the start position and the end position in the light receiving part 130 movement, and the pitch of the in-plane graded scale calculated by the in-plane graded scale calculating part 531 based on the distance-to-object as calculated above. Note that the pitch of the graded scale calculated at the depth graded scale calculating part 532 is designated "the pitch of the depth graded scale".

The generating part 533 generates the three-dimensional graded scale as the graded scale representing the in-plane graded scale and the depth graded scale as combination, based on the distance-to-object calculated at the reflection distance calculating part 513, the pitch of the in-plane graded scale calculated at the in-plane graded scale calculating part 531, and the pitch of the depth graded scale calculated at the depth graded scale calculating part 532. The generated three-dimensional graded scale is output to the graded scale shape correcting part 190.

The operation of the depth graded scale calculating part 532 calculating the space of the depth graded scale and the operation of the generating part 533 generating the three-dimensional graded scale will now be described by referring to FIG. 7 to FIG. 9.

Figure 7:
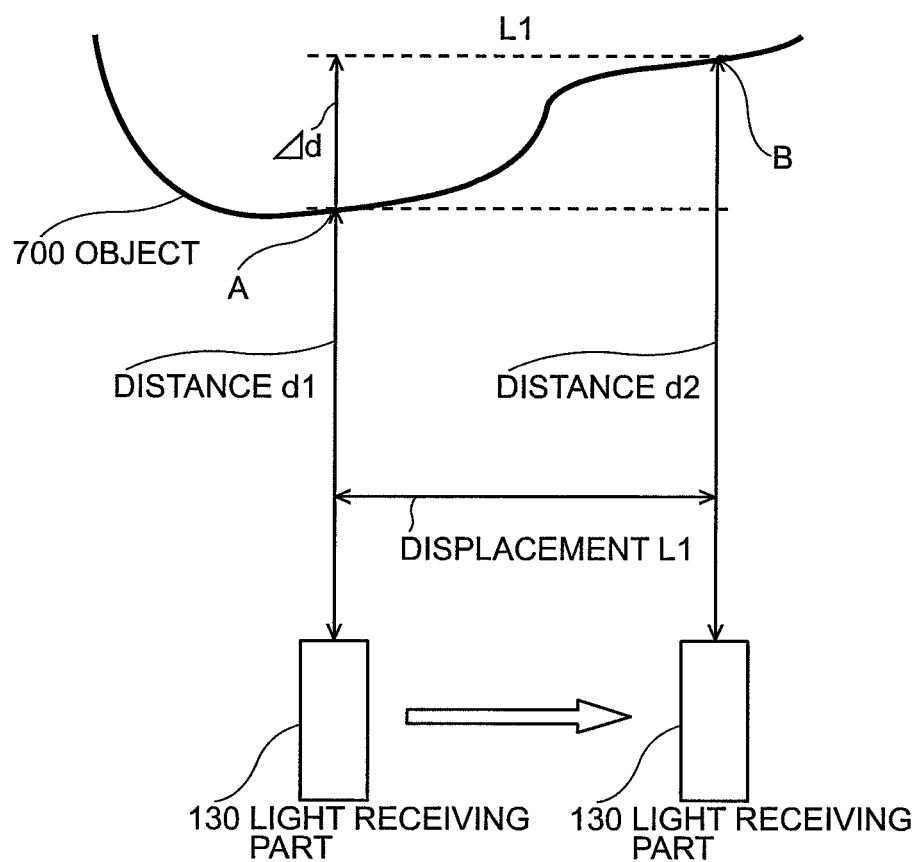
FIG. 7 is an illustration describing one example of the positional relationship between the physical object and the light receiving part 130 shown in FIG. 5.

FIG. 7 is an illustration describing one example of the positional relationship between the physical object and the light receiving part 130 shown in FIG. 5. FIG. 8 is an illustration describing the operation of the depth graded scale calculating part 532 shown in FIG. 6. FIG. 9 is an illustration describing the operation of the graded scale shape correcting part 190 shown in FIG. 5. In this embodiment, FIG. 9 (*a*) shows an example of the three-dimensional graded scale generated by the graded scale generating part 533 and FIG. 9 (*b*) shows an example of the shape-distorted graded scale with its shape being corrected by the graded scale shape correcting part 190.

What will be described below is the operation of the depth graded scale calculating part 532 and the generating part 533 in such a case as shown in FIG. 7 in which the image capturing is started by the light receiving part 130 located at the position opposite to the point A on the physical object so that the light receiving part 130 may face rightly to the physical object and then the light receiving part 130 is moved in parallel to the physical object by the user during a designated period of time to the position opposite to the point B on the physical object.

At first, the depth graded scale calculating part 532, upon the distance-to-object d1 at the point A in FIG. 7 and the pitch m1 of the in-plane graded scale being output as the first output from the in-plane graded scale calculating part 531 shown in FIG. 6, stores those data as the start point data associated with the light receiving part 130 located at the position when starting the movement into the data storing part 200.

Next, the depth graded scale calculating part 532 stores the distance-to-object and the pitch of the in-plane graded scale, which were output from the in-plane graded scale calculating part 531, into the data storing part 200 as the termination point data as the data associated with the light receiving part 130 located at the position after completing the movement, until the displacement accumulating part 523 shown in FIG. 6 outputs the displacement L of the light receiving part 130.

When the displacement L of the light receiving part 130 is output from the displacement accumulating part 523 shown in FIG. 6 after a designated period of time has passed, the depth graded scale calculating part 532 calculates the difference in the distance-to-object caused by the displacement of the light receiving part 130 and the ratio between the pitch of the in-plane graded scale at the start point and the pitch of the in-plane graded scale at the end point, based on the start point data and the end point data stored in the data storing part 200. In this embodiment, the end point data stores the distance-to-object d2 at the point B in FIG. 7 and the pitch m2 of the in-plane graded scale. Thus, the difference between a couple of distances-to-object is calculated as d1−d2=□d, and the ratio of the pitch m1 to the pitch m2 of the in-plane graded scales is calculated as m1/m2 in this embodiment.

Next, the depth graded scale calculating part 532 calculates the layout position of the first in-plane graded scale generated on the basis of the pitch m1 of the in-plane graded scale for the start point data and the second in-plane graded scale generated on the basis of the pitch m2 of the in-plane graded scale for the end point data, both mapped into the captured image, based on the displacement L.

Figure 8:
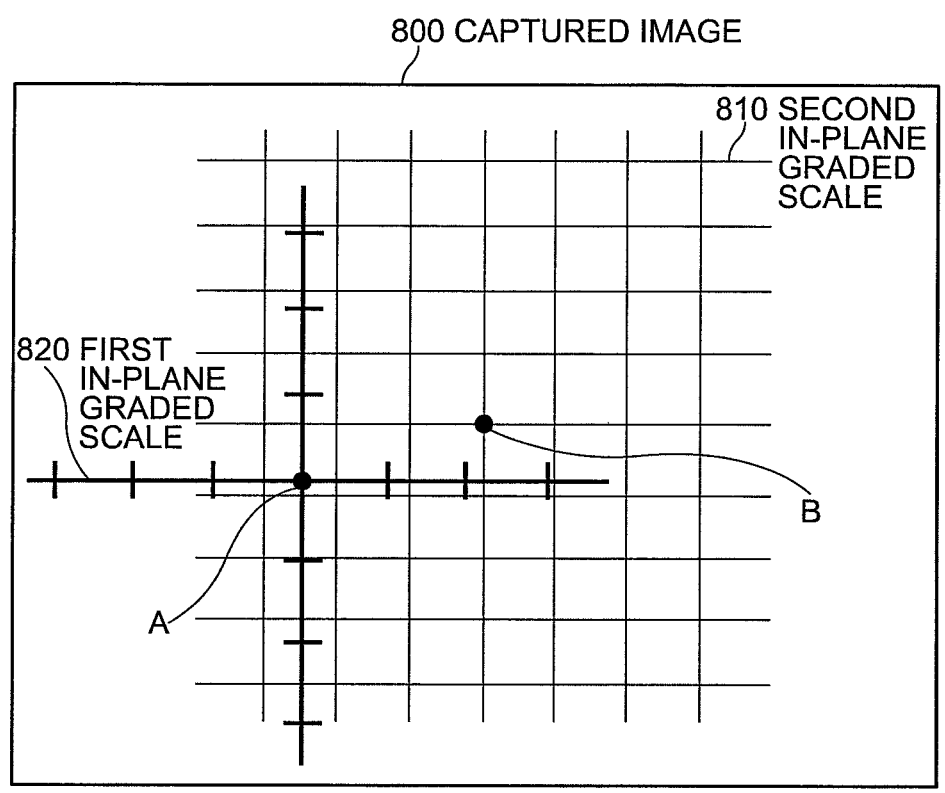
FIG. 8 is an illustration describing the operation of the depth graded scale calculating part 532 shown in FIG. 6.

In this embodiment, as shown in FIG. 8, the center point C of the second in-plane graded scale 820 is aligned to the center position of the captured image 800, and the center point D of the first in-plane graded scale 810 is aligned to the position located by the displacement L from the center of the captured image 800. Note that those positions correspond to the point B and point A on the physical object in the captured image, respectively, in case that there is no distortion aberration at the image capturing optical part 150. Note also that the first in-plane graded scale is illustrated as a cross-hair scale and the second in-plane graded scale is illustrated as a lattice-like graded scale, respectively in FIG. 8, which are only intended to clarify the concept of the present invention, and hence, not illustrated as an over layer onto the actual captured image.

Next, the depth graded scale calculating part 532 calculates the pitch of the depth graded scale based on the layout positions of the first and second in-plane graded scales so calculated in the above manner, the ratio m1/m2 of the pitches of the in-plane graded scales, and the difference □d between the distances-to-object. More specifically, the depth graded scale calculating part 532 calculates the pitch of the depth graded scale, assuming that the length of the line segment connecting between the center point C and the center point D is identical to the difference between the distances-to-object, and that the pitch of the depth graded scale decreases geometrically from the shallower position to the deeper position in the captured image.

Figure 9:
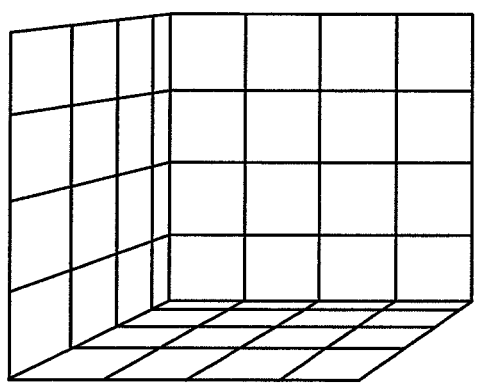
FIG. 9 is an illustration describing the operation of the graded scale shape correcting part 190 shown in FIG. 5.
Figure 9:
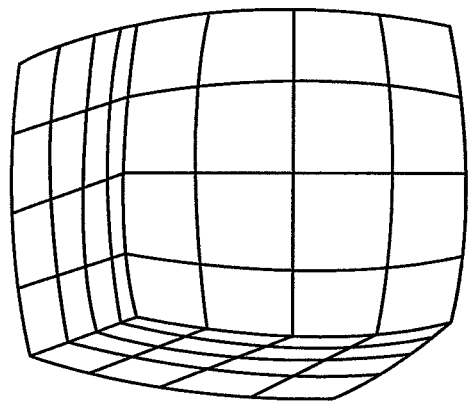

Next, the generating part 533 generates the three-dimensional as shown in FIG. 9 (*a*) based on the calculated pitch of the depth graded scale, the pitch m1 of the in-plane graded scale for the start point data and the pitch m2 of the graded scale for the end point data. The shape of the generated three-dimensional graded scale is corrected at the graded scale shape correcting part 190 and converted to the shape-distorted graded scale as shown in FIG. 9 (*b*). Note that the shape of the three-dimensional graded scale generated by the generating part 533 is not limited to the combined form of the lattice-like graded scale and the L-shaped graded scale as shown in FIG. 9 (*a*) but allowed to be an arbitrary form which enables to recognize the dimension of the physical object in the captured image.

After the depth graded scale calculating part 532 outputs the pitch of the depth graded scale, the start point data and the end point data to the generating part 533, the depth graded scale calculating part 532 stores the end point data as the next start point data at the data storing part 532, and then stores the distance-to-object and the pitch of the in-plane graded scale output from the in-plane graded scale calculating part 531 as the end point data at the data storing part 200.

Figure 10:
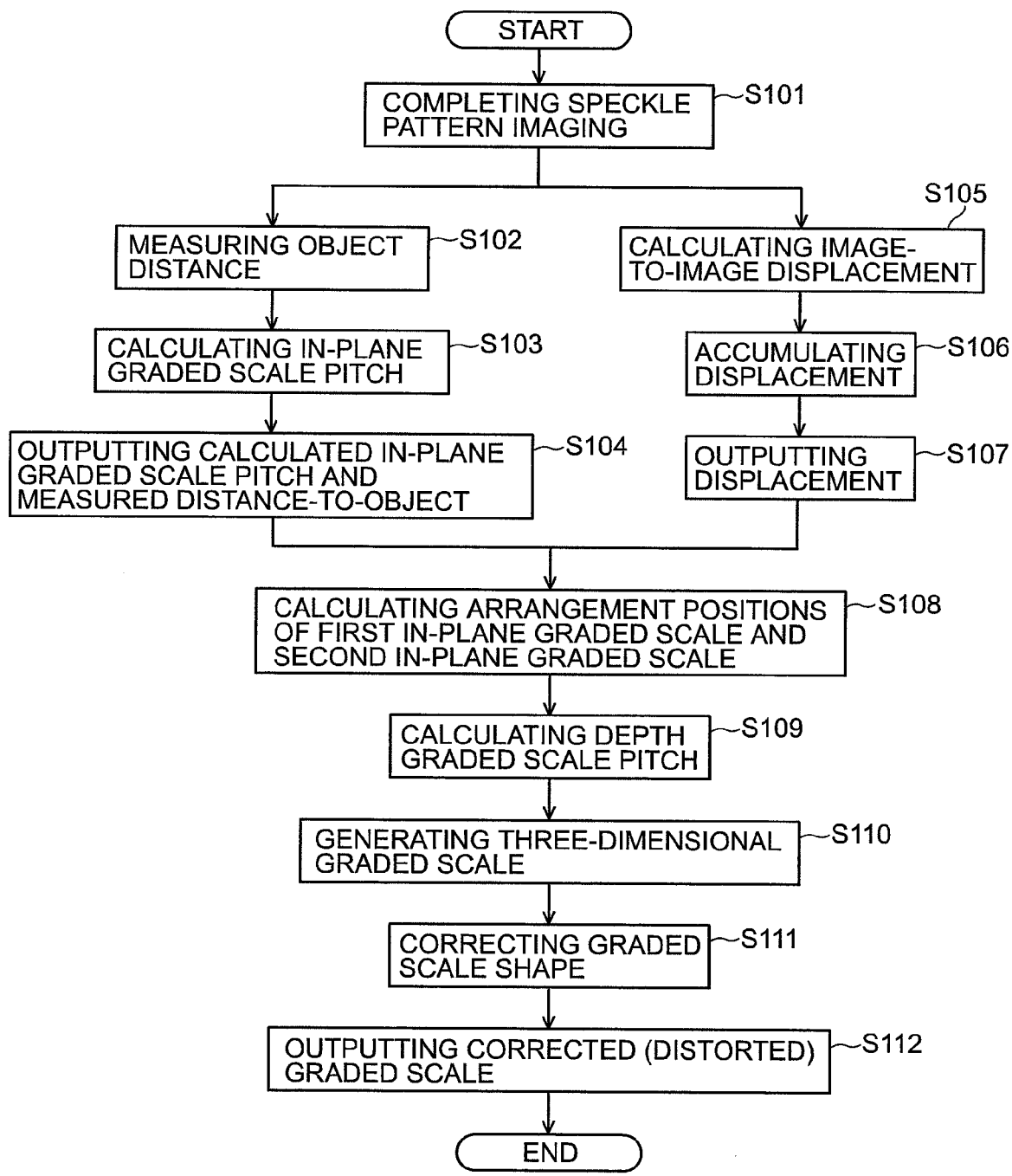
FIG. 10 is a block diagram showing the detail structure of the distance calculating part 510, the displacement calculating part 520 and the graded scale generating part 530 shown in FIG. 5.
Figure 11:
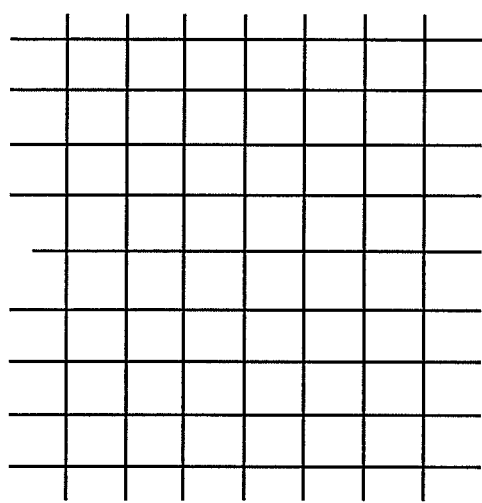
FIG. 11 is an illustration describing the distortion in the object image due to the distortion aberration at the image capturing optical part in the image capturing apparatus.
Figure 11:
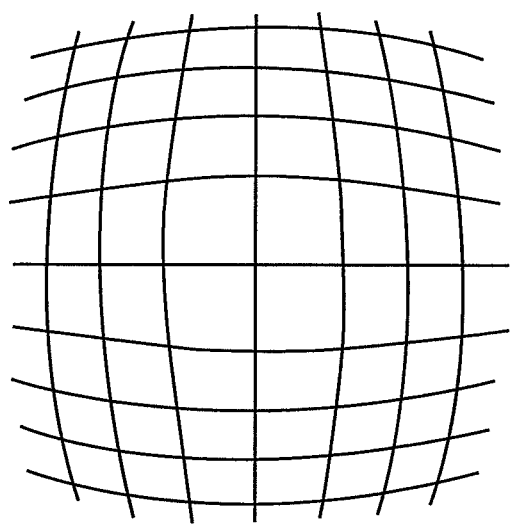

The operation of the image capturing apparatus 500 shown in FIG. 5 will now be described by referring to FIG. 10. FIG. 10 is a flow chart describing the operations of the distance calculating part 500, the displacement calculating part 520, the graded scale generating part 530 and the graded scale shape correcting part 190 shown in FIG. 5. In the followings, the operations related only to Steps S7 to Steps 11 in the flow chart shown in FIG. 4 will be described, and the other operations, which are the same as the operations shown in FIG. 4, will not be described in detail.

At first, the imaging completion optical part 511 of the distance calculating part 510, upon the laser light component, separated from the reflected light reflected at the physical object at the light separating part 140, being injected, completes imaging the speckle pattern as the speckle image at the distance sensor 512 on the basis of the injected laser light component (Step S101).

The distance sensor 512 measures the light income of the laser light component and outputs the measured value to the reflection distance calculating part 513. The reflection distance calculating part 513 calculates the distance-to-object on the basis of the light income output from the distance sensor 512, and then outputs the calculated distance-to-object to the in-plane graded scale calculating part 531 at the graded scale generating part 530 (Step S102).

The in-plane graded scale calculating part 531 calculates the pitch of the in-plane graded scale corresponding to the distance-to-object output from the reflection distance calculating part 513, and then outputs the calculated pitch of the in-plane graded scale and the distance-to-object to the depth graded scale calculating part 532 (Steps S103 and S104). Note that the pitch of the in-plane graded scale and the distance-to-object output to the depth graded scale calculating part 532 are stored by the graded scale calculating part 532 into the data storing part 200 as either the start point data or the end point data.

In turn, the distance sensor 512 also repeats to capture the speckle image on the basis of the frame rate for capturing the speckle image, and then outputs the captured speckle image to the image-to-image displacement calculating part 521 at the displacement calculating part 520. The image-to-image displacement calculating part 521 calculates the displacement between the latest speckle image output from the distance sensor 512 and the previously output speckle image stored at the image storing part 522 (Step S105).

The displacement calculated at the image-to-image displacement calculating part 521 is accumulated at a designated period of time at the displacement accumulating part 523, and the accumulated value is output to the depth graded scale calculating part 532 at the graded scale generating part 530 as the resultant displacement of the light receiving part 130 (Step S106 and S107).

The depth graded scale calculating part 532, upon the resultant displacement of the light receiving part 130 output from the displacement accumulating part 523, calculates the layout positions of the first in-plane graded scale and the second in-plane graded scale in the captured image on the basis of this resultant displacement (Step S108).

The depth graded scale calculating part 532 also calculates the differences in the ratio of the pitches of the in-plane graded scales and the distances-to-object for the start point data and the end point data, respectively, both stored at the data storing part 200, and then, calculates the pitch of the depth graded scale based on these differences and the layout positions of the first in-plane graded scale and the second in-plane graded scale (Step S109).

Next, the generating part 533 generates the three-dimensional graded scale on the basis of the pitch of the depth graded scale, the start point data and the end point data (Step S110).

Next, the graded scale shape correcting part 190, upon the three-dimensional graded scale being generated at the generating part 533, generates the shape-distorted graded scale by applying the shape correction to the three-dimensional graded shape on the basis of the correction matrices stored in the data storing part 200 (Step S111). The graded scale shape correcting part 190 outputs the generated shape-distorted graded scale to the image combining part 210 (Step S112).

The effect of this embodiment will now be described. As described above, in the image capturing apparatus 500 in this embodiment, when the light receiving part 130 is moved by the user, the displacement of the light receiving part 130 is calculated as the vector, the depth graded scale as well as the in-plane graded scale can be generated by way of calculating the pitch of the depth graded scale on the basis of the calculated displacement, a couple of distances-to-object calculated at the start point and the end point for moving the light receiving part 130 by the distance calculating part 510 and the pitch of the in-plane graded scale calculated by the in-plane graded scale calculating part 531. According to this embodiment, it will be therefore appreciated that the dimension of the physical object can be obtained in terms of the three-dimensional geometry from the captured image displayed at the displaying part 220 in the image capturing apparatus 500.

Note that the image capturing apparatus 100 and 500 in Embodiments 1 and 2 as described above are illustrated by way of example, and thus, various modifications in their structure and operation may be made without departing from the scope of the present invention. For example, though the distance-to-object is calculated on the basis of the light income of the laser light component in Embodiments 1 and 2, it is allowed that the pulsed laser light may be irradiated as the laser light 310 from the laser light source 120 and that the distance-to-object may be measured at the distance calculating parts 170 and 510 on the basis of the measured period of time (TOF: Time Of Flight) from the time of the laser light irradiation to the time of the laser reflection light receiving.

Note that some functions of the image capturing apparatus 100 or 500, for example, a part of the distance calculating part 170, the graded scale generating part 180, the graded scale shape correcting part 190, the data storing part 200, the image combining part 210, those included in the image capturing apparatus 100, as well as a part of the distance calculating part 510, the displacement calculating part 520, the graded scale generating part 530, those shown in FIG. 5, the graded scale shape correcting part 190, the image combining part 210 may be constructed as the programs for realizing those functions recorded on the recording medium readable from the image capturing apparatus 100 or 500 and allowed to be read and executed by the image capturing apparatus 100 or 500. The recording medium readable from the image capturing apparatus 100 or 500 may include such a recording media as Floppy (a registered trademark) disk, magneto-optic disk and CD-ROM, and such a recording media mounted inside the image capturing apparatus 100 or 500 as hard disk drive. In addition, the recording medium readable from the image capturing apparatus 100 or 500 may include such a device holding dynamically the program during a definite period of time as volatile memory mounted inside the image capturing apparatus 100 or 500.

What is claimed is:

1. An image capturing apparatus comprising:
    a light receiving part for receiving a reflected light reflected from a physical object;
    an image capturing optical part for completing imaging as an object image by distorting an actual image of said physical object due to distortion aberration in response to said reflected light;
    an image capturing part for capturing said object image as a captured image;
    a displaying part for displaying said captured image;
    a graded scale generating part for generating a graded scale to be used for indicating a dimension of said physical object in said captured image;
    a data storing part for storing data for correction to be used in order to correct a graded scale shape by adding distortion to said generated graded scale in the similar degree to distortion caused by said distortion aberration;
    a graded scale shape correcting part for generating a shape-distorted graded scale by correcting said graded scale shape according to said data for correction;

an image combining part for combining said generated shape-distorted graded scale with said captured image, wherein said displaying part displays said captured image combined with said shape-distorted graded scale;

a laser light source for irradiating a laser light to said physical object;

a light separating part for separating a laser light component as a component of said laser light from said reflected light; and a distance calculating part for calculating a distance-to-object indicating a distance between said physical object and said light receiving part, based on said laser light component, wherein said graded scale generating part comprises:

an in-plane graded scale calculating part for calculating an in-plane graded scale pitch as a pitch of an in-plane graded scale indicating a dimension of said physical object on an identical plane placed at a depth in said captured image equivalent to said distance-to-object; and a generating part for generating said in-plane graded scale based on said graded scale pitch as said graded scale.

2. An image capturing apparatus in claim 1, wherein said distance calculating part comprises:

a distance sensor for measuring a light income indicating an intensity of said laser light component; and a reflection distance calculating part for calculating said distance-to-object based on said light income.

3. An image capturing apparatus as claimed in claim 2, further comprising:

a movement calculating part for calculating a movement of said light receiving part as a first vector moved by a user of said image capturing apparatus during a definite period of time, wherein said graded scale generating part comprises:

a depth graded scale calculating part for calculating a pitch of a depth graded scale to be used as an index of a dimension of said physical object in said captured image, based on said movement, said distance-to-object calculated by said distance calculating part at a start position and an end position of said movement, and a pitch of an in-plane graded scale calculated by said in-plane graded scale calculating part based on the distance-to-object at said two points, wherein said generating part for generating said in-plane graded scale based on said pitch of said in-plane graded scale as said graded scale also generates said depth graded scale based on said pitch of said depth graded scale and said movement as said graded scale in addition to said in-plane graded scale.

4. An image capturing apparatus as claimed in claim 3, further comprising an operating part for accepting an instruction from said user, wherein said movement calculating part calculates said movement of said light receiving part during a period of time from a time when an instruction for starting said movement is received at said operating part to a time when an instruction for ending said movement is received, instead of said definite period of time.

5. An image capturing apparatus as claimed in claim 3, wherein said distance calculating part comprises an imaging completion optical part for completing imaging of a speckle pattern as a speckle image developed on said physical object by irradiating said laser light based on said laser light component, said distance sensor repeats to capture said speckle image; and said movement calculating part comprises an image-to-image displacement calculating part for calculating a displacement between successive speckle images captured by said distance sensor as a vector; and a displacement accumulating part for calculating said movement by accumulating said displacement between a couple of said movement.

* * * * *